United States Patent
Mathisen et al.

(10) Patent No.: US 9,717,704 B2
(45) Date of Patent: Aug. 1, 2017

(54) METHOD OF TREATING, DELAYING AND/OR PREVENTING ALZHEIMER'S DISEASE

(71) Applicant: Smartfish AS, Oslo (NO)

(72) Inventors: Janne Sande Mathisen, Oslo (NO); Henrik Mathisen, Oslo (NO)

(73) Assignee: Smartfish AS, Oslo (NO)

( * ) Notice: Subject to any disclaimer, the term of this patent is extended or adjusted under 35 U.S.C. 154(b) by 0 days.

(21) Appl. No.: 14/304,108

(22) Filed: Jun. 13, 2014

(65) Prior Publication Data

US 2015/0031653 A1 Jan. 29, 2015

Related U.S. Application Data

(60) Provisional application No. 61/834,455, filed on Jun. 13, 2013.

(51) Int. Cl.

| | |
|---|---|
| *A61K 31/202* | (2006.01) |
| *A61K 31/07* | (2006.01) |
| *A23L 2/52* | (2006.01) |
| *A61K 9/107* | (2006.01) |
| *A61K 31/05* | (2006.01) |
| *A61K 31/593* | (2006.01) |
| *A61K 35/60* | (2006.01) |
| *A61K 36/73* | (2006.01) |
| *A61K 31/375* | (2006.01) |
| *A23L 33/105* | (2016.01) |
| *A23L 33/115* | (2016.01) |
| *A23L 33/12* | (2016.01) |

(52) U.S. Cl.
CPC .......... *A61K 31/202* (2013.01); *A23L 2/52* (2013.01); *A23L 33/105* (2016.08); *A23L 33/115* (2016.08); *A23L 33/12* (2016.08); *A61K 9/107* (2013.01); *A61K 31/05* (2013.01); *A61K 31/375* (2013.01); *A61K 31/593* (2013.01); *A61K 35/60* (2013.01); *A61K 36/73* (2013.01); *A23V 2002/00* (2013.01)

(58) Field of Classification Search
CPC ............................ A61K 31/10; A61K 31/095
USPC .................................................. 514/167, 560
See application file for complete search history.

(56) References Cited

U.S. PATENT DOCUMENTS

| | | | |
|---|---|---|---|
| 4,897,388 A * | 1/1990 | Malluche | A61K 31/59 514/167 |
| 6,184,248 B1 * | 2/2001 | Lee et al. | 514/474 |
| 8,491,953 B2 | 7/2013 | Mathisen et al. | |
| 2008/0286414 A1 | 11/2008 | Mathisen et al. | |
| 2009/0074933 A1 | 3/2009 | Mathisen et al. | |
| 2009/0202679 A1 | 8/2009 | Mathisen | |
| 2011/0135745 A1 | 6/2011 | Mathisen et al. | |

FOREIGN PATENT DOCUMENTS

| | | |
|---|---|---|
| WO | 2006/043830 A1 | 4/2006 |
| WO | 2007/001185 A1 | 1/2007 |
| WO | 2007/064222 A1 | 6/2007 |
| WO | WO 2009/120091 A1 * | 10/2009 |

* cited by examiner

*Primary Examiner* — Jennifer M Kim
(74) *Attorney, Agent, or Firm* — Fitzpatrick, Cella, Harper & Scinto

(57) ABSTRACT

The present invention relates to the treatment and/or prevention of Alzheimer's Disease or the symptoms associated therewith by daily administration of a drink formula comprising fresh marine omega-3 oil in an emulsion and resveratrol or derivatives thereof.

22 Claims, 15 Drawing Sheets

Group 1 AD: Change in Baseline Expression of Inflammatory Genes

Fig. 3

Group 1 AD:

Change in the effect of exogenous pathogens (sA$\beta_{1-42}$)

Group 1 AD: Change in the effect of exogenous pathogen (sA$\beta_{1-42}$)

Group 2 AD phagocytosis of FAM-Aβ

- (+/-): 2 μg/ml FAM-Aβ$_{(1-42)}$ [Green], marginal increase in Abeta binding following Drink Formulation of Example 1

In vitro Group 2 AD phagocytosis of FAM-Aβ

Untreated (−/−)　　+FAM-Aβ$_{(1-42)}$ (+/−)　　+FAM-Aβ + 0.55 mg/ml Example 1 (+/+)

- (−/−): At baseline pSTAT3 localized to cytosol
- (+/−): 2 μg/ml FAM-Aβ$_{(1-42)}$ [Green]
- (+/+): 0.055 mg/ml treatment enhanced binding of FAM-Aβ$_{(1-42)}$ [Green]

Effect of Drink Formulation of Example 1 on STAT3 Localization in a Group 2 AD Patient

- (−/−): At baseline pSTAT3 localized to cytosol
- (+/−): 2 μg/ml sAβ$_{(1-42)}$ induces a strong nuclear translocation of pSTAT3
- (+/+): 0.055 mg/ml treatment which attenuates the translocation of pSTAT3 to the nucleus Group 2AD/Controls: Baseline

Fig. 9
Group 2 AD: Effect of Drink Formulation of Example 1
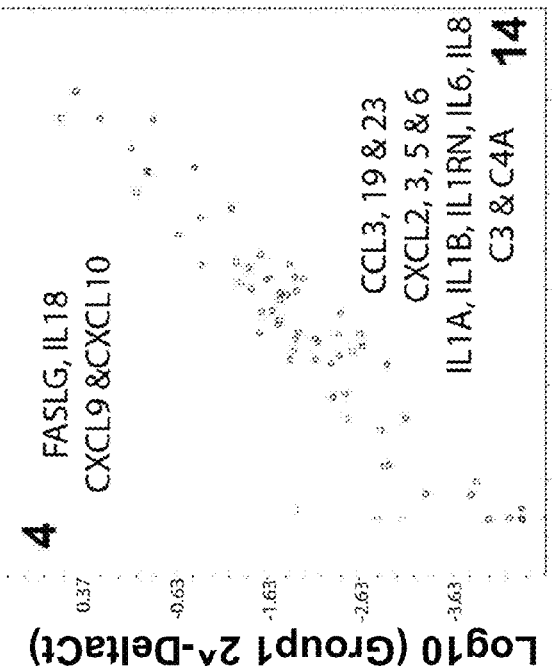
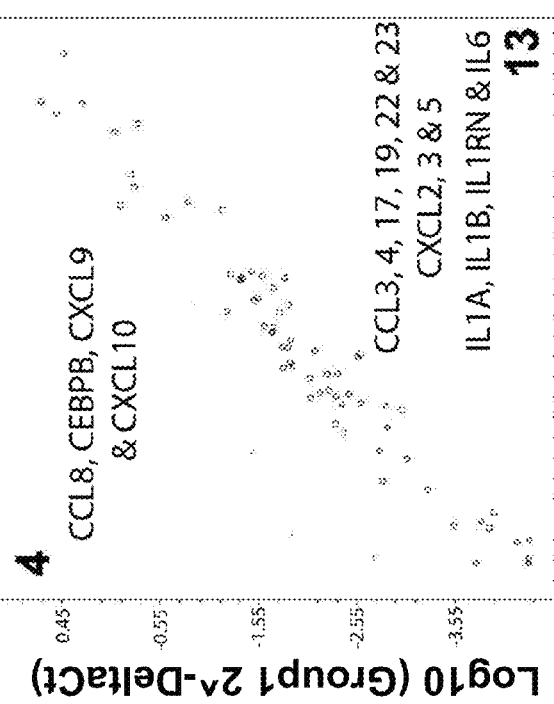

METHOD OF TREATING, DELAYING AND/OR PREVENTING ALZHEIMER'S DISEASE

RELATED APPLICATION

This application claims the benefit of priority of U.S. Provisional patent application No. 61/834,455, filed on Jun. 13, 2013, the contents of which are incorporated by reference.

BACKGROUND OF THE INVENTION

Field of the Invention

The present invention relates to a method of treating, delaying and/or preventing Alzheimer's Disease (AD) by administering a formulation comprising fresh marine omega-3 oil in an emulsion and resveratrol or derivatives thereof to a human.

Description of Prior Art

The health promoting effects of polyunsaturated oils are well known. The health promoting effects of antioxidants are also known. WO2009/120091 discloses a composition combining these nutrients in a formula that result in increased absorption and where the body is able to utilize the nutrients optimally. The disclosed compositions provide formulations where these native unstable health promoting nutrients are kept intact and fresh.

The effects of omega-3 fatty acids (EPA, DHA and DPA) on a number of diseases and conditions, such as cardiovascular, mental, skin and ageing, are well documented. Supplementation of omega-3 increases world wide. There is an increase in the consumption of omega-3 containing products, and omega-3 in the form of fish and/or food supplement is highly recommended by health authorities.

Oxidative stress is a sort of "chemical stress" induced by the presence in our body of abnormal quantities of free radicals. Whatever the cause, oxidative stress is believed to be responsible of early ageing and of a very long series of common diseases—about one hundred—that span from arterial hypertension to atherosclerosis, from infarct to ictus, from Parkinson's to Alzheimer's, from colitis to pancreatitis, from obesity to diabetes, from chronic bronchitis to rheumatoid arthritis, from AIDS to several types of cancer.

The body is protected against free radicals by antioxidants, both self-produced and antioxidants supplied through food and drinks. Antioxidants may be vitamins, minerals, and enzymes, either fat soluble or water soluble.

In situations where the body is subjected to enhanced oxidation (a lot of free radicals), the body might not have sufficient antioxidants to neutralize or quench the free radicals. Destructive chain reactions occur, which might cause increased and detrimental oxidative stress.

The theoretical basis for the effects of antioxidants is well acknowledged. It is also acknowledged that the absorption of antioxidants in the body from antioxidant supplements is a challenge. However, studies have demonstrated that antioxidants in a non-native form or as isolated vitamins are inadequately taken up by the body. Some studies indicate that ingestion of high dosages of isolated vitamins may convert antioxidants to prooxidants, thus leading to elevated oxidation in the body. Studies and literature indicates better absorption and bioavailability of antioxidants naturally present when consumed in foods e.g. as fruits and vegetables.

It is known that humans having severe oxidative stress are often deficient in omega-3 fatty acids (DHA and EPA), and possess a low antioxidative status.

Oxidative damage and antioxidant deficiency are now regarded as crucial factors to many diseases, and are probably the primary reason for an imperfect replacement of old damaged cells by new cells.

Research work has demonstrated that oxidation products of fatty acids are highly reactive and may affect and interfere with intracellular processes. Many commercially available omega-3 supplements contain fish oil having a significant degree of oxidation, which in turn may induce adverse effects on intracellular processes.

Although these dietary supplements often are added antioxidants, this will not reverse the rancidity already present in the dietary supplement. On the other hand, to prevent further oxidation of the unsaturated fish oil, the antioxidants in the supplement will be consumed and finally (after some months) cease. In this case, antioxidants in such commercially available dietary supplements will not induce any health promoting effects in humans.

WO2009/120091 provides advantageous compositions combining fresh fish oil and specific antioxidants to provide a new drink formula having improved health promoting effects on humans. There is, however, no disclosure of treating, delaying and/or preventing Alzheimer's Disease with a composition comprising marine oil and resveratrol.

Alzheimer's Disease (AD) is the most prevalent form of dementia. AD impacts millions of people worldwide and at present there is no known cure for the disease. The symptoms of Alzheimer's Disease become progressively more debilitating as the disease advances. Ultimately, Alzheimer's Disease results in the death of the inflicted individual, typically after many years of gradually losing the ability to function in society. Thus, there is a significant need for a treatment to prevent, delay and/or treat Alzheimer's Disease.

SUMMARY OF THE INVENTION

The present invention is directed to a method of preventing and/or treating Alzheimer's Disease in humans by administering a formulation comprised of fresh marine oil and the antioxidant, resveratrol or derivatives thereof. In a preferred embodiment the formulation is a drink. In one embodiment, the method is directed to preventing and/or delaying the onset of the symptoms of Alzheimer's Disease in a person by administration of the formulation described herein. In another embodiment, the method is directed to treating a person suffering from the symptoms associated with Alzheimer's Disease by administration of a formulation described herein. Preferably the formulation is administered in the method of this invention on a daily basis, and most preferably it is a drink formulation administered on a daily basis. As used herein daily basis means administering at least once a day, but also includes multiple administrations in a day, e.g. twice or thrice daily.

BRIEF DESCRIPTION OF THE DRAWINGS

FIG. 3 illustrates the change in the effect of the exogenous pathogen ($sA\beta_{1-42}$) in Group 1 AD patients after 3 month's administration of the drink formulation.

FIG. 9 illustrates a comparison of inflammation in AD patient Group II on a daily regimen of Example 1 drink formulation compared to inflammation in two patients in group 2 who were non-compliant with administration of the drink formulation.

FIG. 10A includes results for cognitively normal subjects or caregivers where RB and DS are care givers; CE is a Parkinson disease patient; DN is a diabetic patient with normal cognition; EB is a patient with ALS; and MF and FD are normal controls. FIG. 10B includes results for cognitively-impaired patients with MMSE ≤19 at baseline receiving supplementation with the omega-3 drink with antioxidants supplemented with resveratrol (Smartfish drink) after the first visit. FIG. 10C includes results for patients with Alzheimer's disease (MMSE≤19) receiving supplementation with the omega-3 drink with antioxidants supplemented with resveratrol (Smartfish drink).

DESCRIPTION OF PRESENT INVENTION

Figure 1:
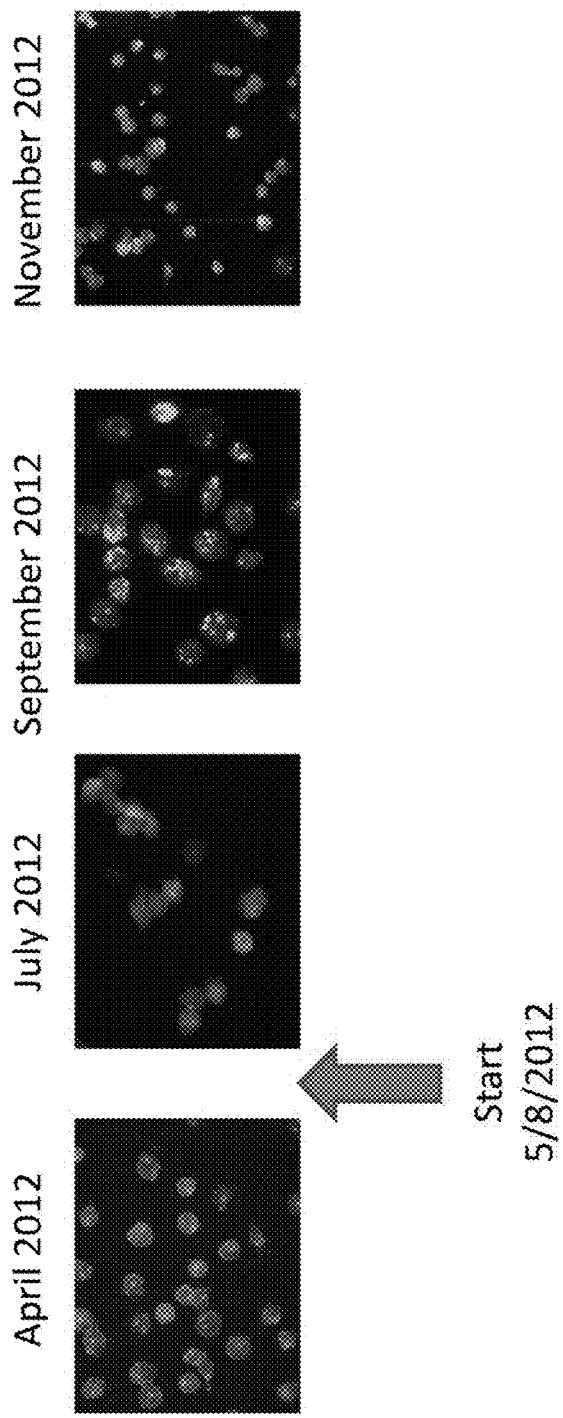
FIG. 1 illustrates the improved phagocytosis of amyloid beta after administration of the drink formulation of Example 1 to AD patients (Group 1) showing down regulation of inflammatory genes.

The formulation used in the methods of the invention is a combination of fresh marine oil and resveratrol or derivatives thereof. Preferably the formulation is a drink formulation, although it is also contemplated that the formulation may be presented in other well-known administrative forms, such as a tablet or capsule or gel. For example, a drink formulation may be prepared and then dried, e.g. lyophilized to a powder or granulation, and then presented in a tablet or capsule dosage form. Alternatively, the drink formulation could be concentrated to form a concentrate for use by a patient or gelled using standard gelling techniques to provide an edible gel.

Preferably, the drink formulation may have a base containing natural antioxidants e.g. fruit or vegetable juice, green tea, but any drinkable liquid may be used. Most preferably the base is a fruit juice, such as, for example, those selected from the group consisting of apple concentrate, pear concentrate, pomegranate concentrate, chookberry concentrate and combinations thereof.

The drink formulation combines a stable omega-3 emulsion known from the prior art, and resveratrol or derivatives thereof. Preparation of the drink formulation used in the method of the present invention is described in US2011/0135745, the disclosure of which is incorporated by reference herein in its entirety. Such drink formulations show improved delivery, improved uptake and improved effect on oxidative stress.

Both the omega-3 oil and the antioxidants contained in the drink used in the method of this invention are remarkably stable in the composition, and the progress of rancidity and loss of antioxidant effects are much lower than in known product formulated as separate capsules.

One aspect of the present invention relates to the unexpected and surprising discovery that a drink formulation comprising fresh marine oil in an oil-in-water emulsion wherein the marine oil has a totox value below 15, with a further added at least one antioxidant, of resveratrol (3,5,4'-trihydroxy-trans-stilbene) which is not naturally present in said oil-in-water emulsion, provides a drink formulation that shows promise in the treatment and/or prevention of Alzheimer's Disease and/or the symptoms associated therewith. As used herein, treatment includes delaying the advance or onset of symptoms of AD, arresting the development of symptoms AD and/or reversing the symptoms associated with AD. As used herein, preventing means delaying the onset of the symptoms in AD in a person susceptible to AD, e.g., a person at least 55 years old, preferably at 60 years old, more preferably at least 65 years old. As used herein, Alzheimer's Disease and/or the symptoms associated therewith include minor cognitive impairment (MCI).

As used herein, derivatives of resveratrol include for example hydrolyzable derivatives such as esters, e.g. C1-6 alkyl esters, of one or more of the hydroxyl groups of resveratrol.

The term fresh marine oil describes an oil prepared from fresh fish where all process steps are conducted carefully and under strict oxygen control according to functional oil standards in order to prevent oil oxidation. The fresh marine oil will have a low oxidative status, revealing a colourless oil without the characteristic smell or taste of fish. The level of oxidation given as the totox value (2 times the peroxide value (PV) added with the anisidin value (AV)) should be below 15, preferably below 10, and most preferably below 5. Marine oil present in many food supplements today contains oil with a much higher totox value, typically 20-30 or even higher.

The fresh marine oil may be any oil rich in omega-3, e.g. fish oil, seal oil or hill oil. The oil may be mixed with other polyunsaturated oils of vegetable origin such as algae oil and herbal oil such as evening primrose oil and rapeseed oil.

In one preferred embodiment of the present invention the drink formulation is comprised of marine oil, in an amount of about 0.5% to about 10% by weight based on the total weight of the drink formulation, more preferably in the range of, about 0.5% to about 7%, most preferably in the range of about 1.5% to about 4%.

The oil-in-water emulsion is prepared by any conventional method, preferably as described in the applicants own Norwegian applications NO 20044542, 20053136 and 20055620. In said emulsions the antioxidants are present to stabilize the oil during production and storage, not for the purpose of inducing any health promoting effects on humans.

The water phase of the oil-in-water emulsion is preferably a water phase containing natural antioxidants e.g. fruit/vegetable juices, green tea, white tea and herbal tea. The juice may be a fresh pressed juice or juice in the form of juice concentrate or juice puree, or purée diluted to obtain a normal ready-to-use juice. The water phase may also contain proteins such as soy, oat proteins, whey proteins and/or milk proteins. The drink formulation will generally have added water in the amount of about 50 to about 90 weight percent, preferably about 60 to about 80 weight percent. When fruit juice concentrate is added, the drink formulation will contain about 5 to about 30 weight percent fruit juice concentrate, preferably about 10 to about 20 weight percent fruit juice concentrate.

It has been surprisingly discovered that a drink formulation containing the fresh marine oil described above in combination with resveratrol or derivatives thereof, may have a beneficial impact on symptoms associated with Alzheimer's Disease or the treatment and/or prevention of Alzheimer's Disease.

Preferably the resveratrol is present in the drink formulation in an amount of about 0.01 to about 0.5 percent by weight of the formula, more preferably about 0.05 to about 0.25 percent by weight of the formula. In a particular preferred embodiment of the invention a one serving drink formulation contains about 130 mg of resveratrol.

In one embodiment, the formulation may also include one or more vitamins such as, for example, vitamin B, C and/or D and/or one or more minerals such as, for example, selenium, folic acid and/or zinc.

In one embodiment of the present invention, the drink used may also include prebiotics and/or probiotics.

In one embodiment of the present invention, the drink used may be carbonated.

The drink formulation may be prepared, for example, by the following steps:

a) resveratrol and flavoring agents, together with emulsifier are added to the oil phase, b) water soluble additives are added to the water phase, c) the oil and water phase are mixed to a homogenous emulsion, d) the emulsion obtained is optionally subjected to pasteurization and/or homogenization processes, e) the obtained emulsion is cooled down and filled on clean disposable containers;

wherein all steps are performed under strict oxygen control.

Alternatively, in yet another example, the drink formulation may be prepared according to the following steps:

a) transresveratrol and flavoring agents are added to the oil phase, b) water soluble additives are added to the water phase, c) the oil and water phase are mixed and the emulsifier is added, followed by gentle mixing to achieve a homogenous emulsion, d) the emulsion obtained is optionally subjected to pasteurization and/or homogenization processes, e) the obtained emulsion is cooled down and filled on clean disposable containers;

wherein all steps are performed under strict oxygen control.

In the present invention the drink formulation described herein has been found to show properties that suggest it will be useful in the prevention and/or treatment of Alzheimer's disease. In particular, it has been discovered that individuals drinking the drink formulation described herein on a daily basis showed an improvement in inflammatory gene transcriptions in AD patients. In particular, it was found that the macrophages of the AD patients received the ability to phagocyte amyloid beta. Defective phagocytosis of amyloid beta is a well-known marker of AD.

The specific drink formulation used in the method of the invention is believed to provide significant advantages to humans to which it is administered, including, presenting the essential nutrients and specific health promoting agents (polyunsaturated fatty acids and added antioxidants) to the digestive system and to the cells in a format highly beneficial to the cells and the body.

While the method of the invention is preferably practiced by administration of a drink formulation, it is also contemplated that the drink formulation could be administered concentrated or dried to a granulation or powder. Such a granulation or powder could be formed into a tablet or placed in a capsule using well known procedures. Alternatively the formulation for administration in the method of the invention could take the form of a gel or concentrate that may be prepared from the drink formulation by respectively, employing one or more standard gelling agents or preparing the formulation as a concentrate.

The drink formulation may be administered on a daily basis in a volume range of 50-300 ml, preferably 100 ml and more preferably 200 ml. The range of each of DHA and EPA in the drink formulation that is administered may be from about 500 mg to about 5000 mg per day, preferably about 3000 mg per day, more preferably about 2000 mg per day and most preferably about 1000 mg per day. Generally, the range of resveratrol in the administered formulation may be from about 20 to about 800 mg per day, preferably about 50 to about 600 mg per day, more preferably about 75 to about 300 mg per day and most preferably about 130 mg.

EXAMPLES

The invention will now be further illustrated with reference to the following non-limiting examples.

Example 1

A 200 ml drink formulation providing about 1000 mg of each of EPA and DHA per day along with 130 mg per day of resveratrol was prepared from a fresh marine oil omega-3 emulsion and resveratol.

|  | wt. % |
| --- | --- |
| Water, purified | 74.3 |
| Pomegranate | 3.5 |
| Chookberry | 1 |
| Vitamin $D_3$ (10 γg) | — |
| Whey Protein Isolate | 4.2 |
| Fiber | 0.5 |
| Apple Juice Conc. | 6 |
| Pear Juice Conc. | 5 |
| resveratrol (130 mg) | 0.065 |
| Marine oil | 4.8 |
| DHA & EPA 1000 mg each |  |
| sum | 100.00 |

Example 2

Peripheral blood mononuclear cells (PBMCs) of AD patients show either up regulation (Group 2) or down regulation (Group 1) of inflammatory genes in comparison to age-matched controls at baseline, but PBMCs of all AD patients are stimulated by amyloid beta (Abeta) to inflammation. A universal biomarker of AD patients is defective phagocytosis of soluble or fibrillar Abeta by macrophages. In vitro, the lipid modulator from docosahexaenoic acid (DHA) resolvin D1 (RvD1) and the hormonal form of vitamin D3 1,25dihydroxyvitamin D3 (1,25D3) repair the deregulation of these genes and Abeta phagocytosis (Mizwicki T et al. JA1z Dis 2013). DHA and vitamin D3 are frequently taken as nutritional supplements against dementia, but their biochemical effects in vivo are not well known. Example 1 is a drink formula comprised of marine oil contrary with DHA and eicosapentaenoic acid (EPA) stabilized against oxidation through additive and synergistic effects of components from plants (pomegranate and chookberry), vitamin D3, transresveratrol, whey protein isolate and fiber. The inflammatory gene transcription in AD patients who have been consuming this drink daily for over 8 months was tested. In the Group 1 patients the transcription of IL-1 beta increased whereas in the Group 2 IL-1 beta transcription decreased, and the macrophages from both groups recovered the ability to phagocytize Aβ. Minimental state examination (MMSE) scores were stabilized. In conclusion, it was found that nutritional supplementation with a drink containing DHA, EPA, vitamin D3 and other components corrects abnormal transcription and recovers Aβ phagocytosis in AD patients.

Figure 2:
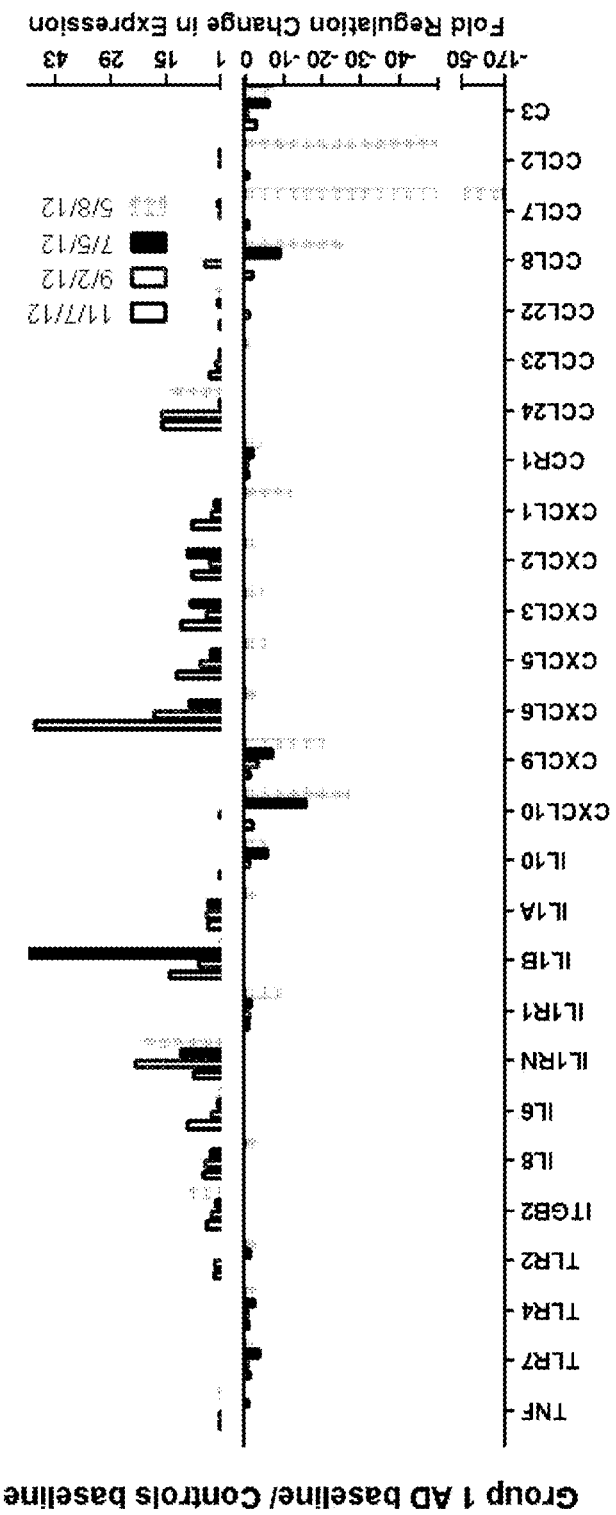
FIG. 2 illustrates the change in baseline expressions of inflammatory genes after administration of the drink formulation of Example 1 to Group 1 AD patients.
Figure 4:
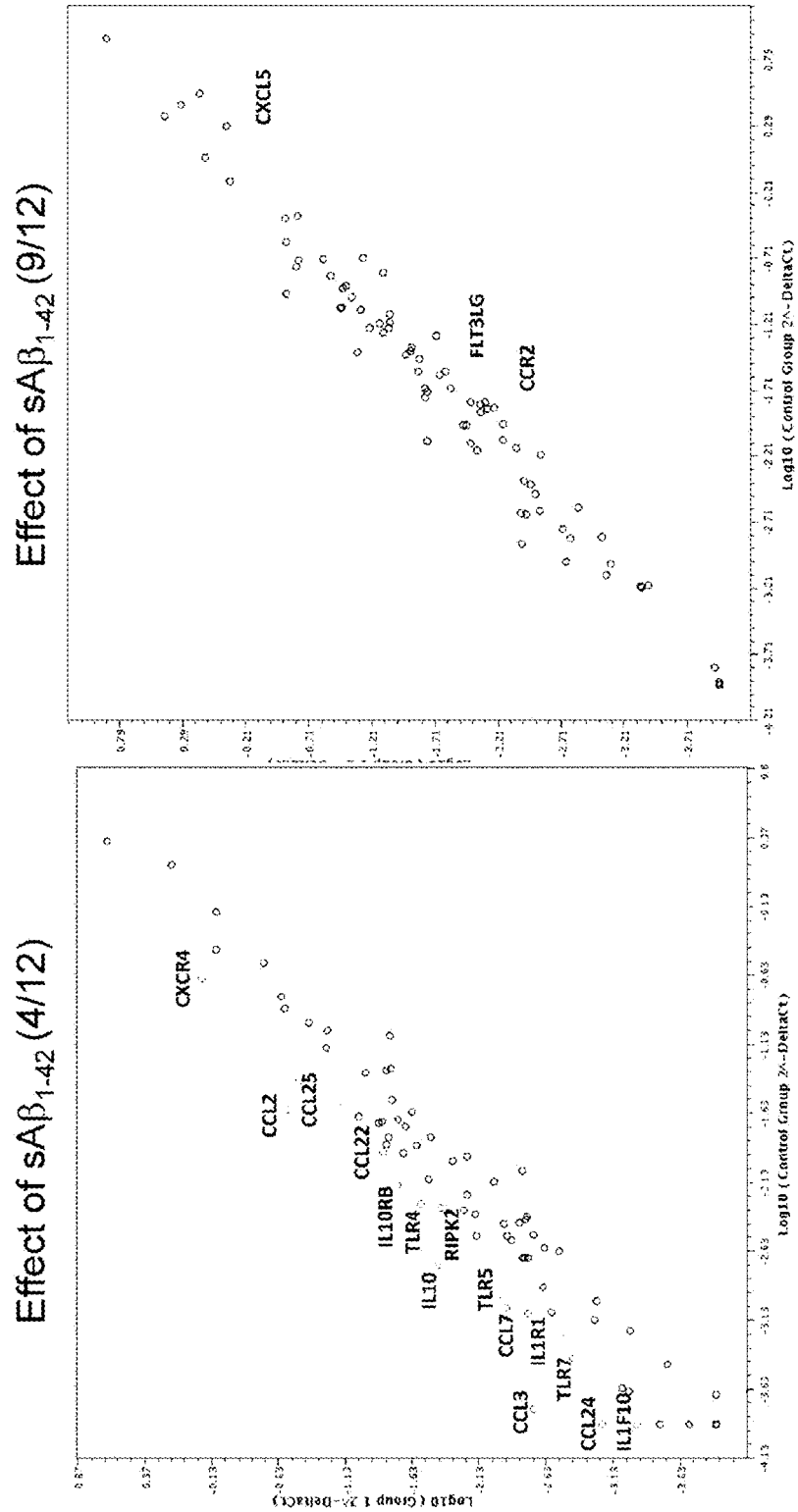
FIG. 4 illustrates the change in the effect of the exogenous pathogen (sAβ$_{1-42}$) in Group 1 AD patients after 5 month's administration of the drink formulation.
Figure 5:
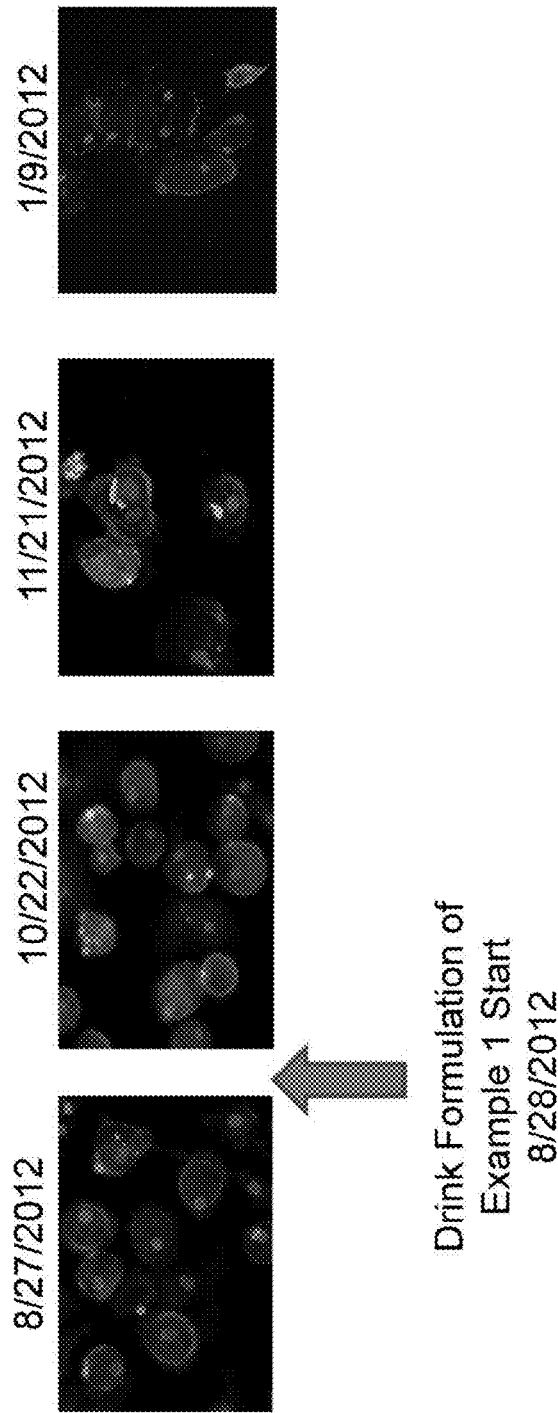
FIG. 5 illustrates the improved phagocytosis of amyloid beta after administration of the drink formulation of Example 1 to AD patients (Group 2) showing up regulation of inflammatory genes.
Figure 6:
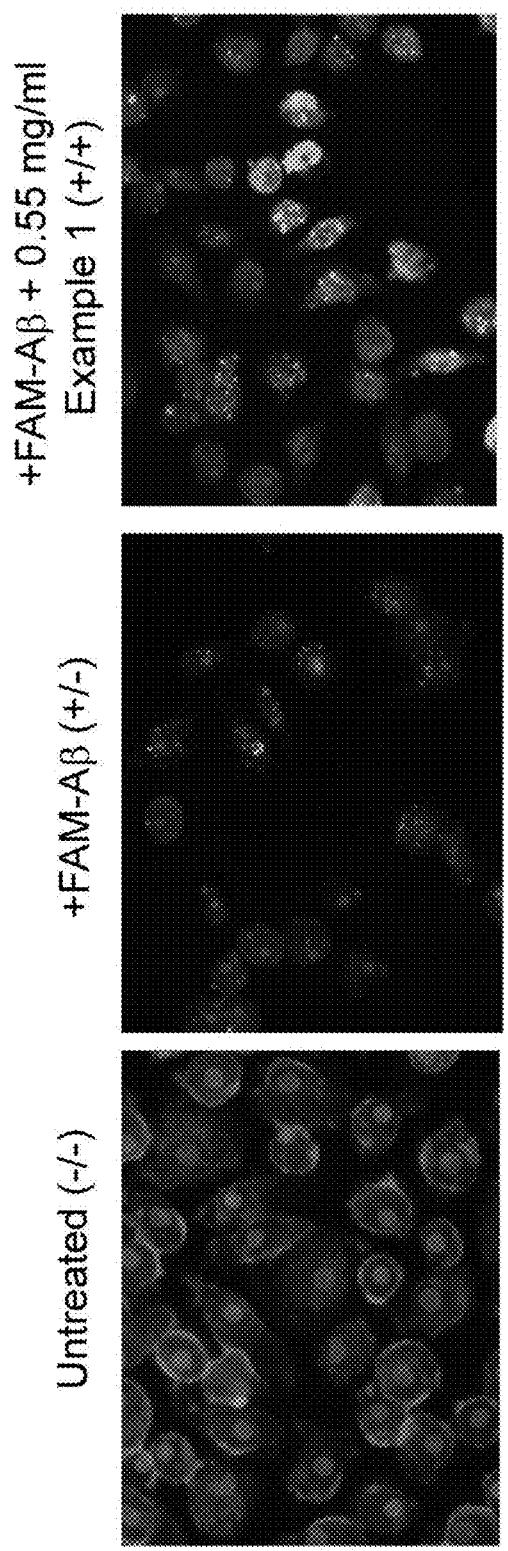
FIG. 6 illustrates macrophages obtained from Group 1 and Group 2 patients.
Figure 7:
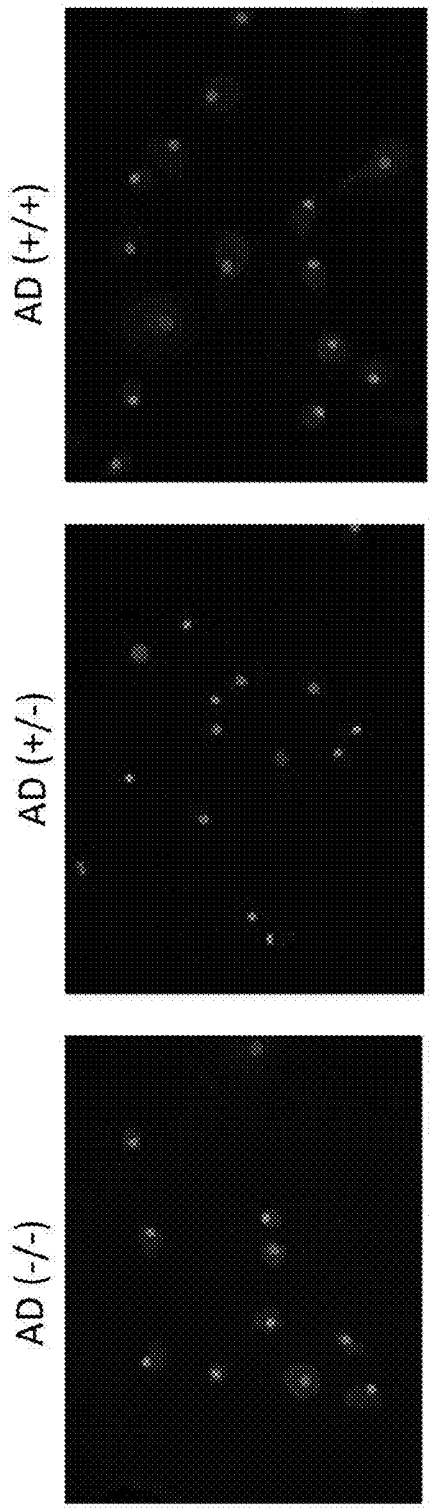
FIG. 7 illustrates the results of patient G from Group 2 after treatment with the drink formulation of Example 1.

FIG. 1 illustrates the effect of Example 1 drink formulation on Group 1 AD phagocytosis of FAM-Aβ while FIG. 2 shows the change in baseline expression of inflammatory genes. In particular, FIG. 2 illustrates an up regulation in the expression of most genes in the Group 1 AD PBMCs had been observed after using the example 1 drink formulation (5/18/12). FIG. 3 illustrates the change in the effect of the exogenous pathogen (sA$\beta_{1-42}$) in Group 1 AD patients after 3 month's administration of the drink formulation of Example 1, while FIG. 4 illustrates the change in the effect of the exogenous pathogen (sA$\beta_{1-42}$) in Group 1 AD patients after 5 month's administration of the drink formulation of Example 1. FIG. 5 illustrates the improved phagocytosis of amyloid beta after administration of the drink formulation of Example 1 to AD patients (Group 2) showing up regulation of inflammatory genes. FIG. 6 illustrates macrophages obtained from Group 1 and Group 2 patients. FIG. 7 illustrates the results of patient G from Group 2 after treatment with the drink formulation of Example 1.

Figure 8:
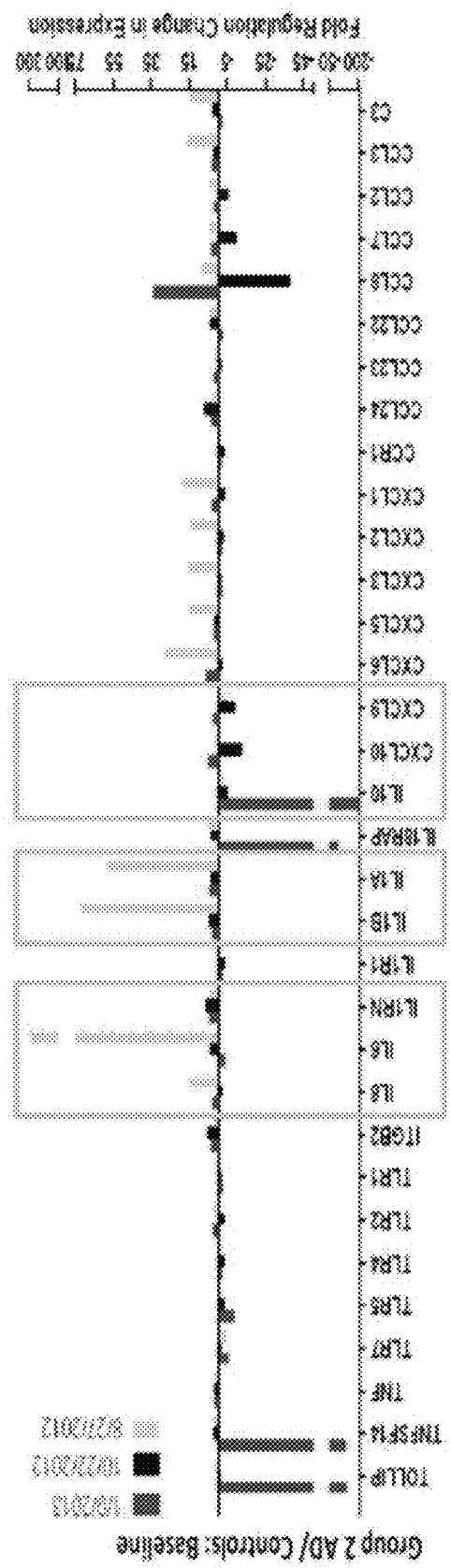
FIG. 8 illustrates the change in baseline expression of inflammatory genes after administration of the drink formulation of Example 1 to Group 2 AD patients.

FIG. 8 illustrates the change in baseline expression of inflammatory genes after administration of the drink formulation of Example 1 to Group 2 AD patients. A down regulation in the expression of most genes in the Group 2 AD PBMCs was observed following use of the drink formulation of Example 1 which was started on Aug. 28, 2012. Nearly all of the genes down on Jan. 9, 2013 were potently up regulated when the PBMCs were challenged with exogenous sA$\beta_{1-42}$. FIG. 9 illustrates a comparison of inflammation in AD patient Group II on a daily regimen of Example 1 drink formulation compared to inflammation in two patients in group 2 who were non-compliant with administration of the drink formulation. Over a one year period at least two follow-ups were conducted with three Group 2 or high baseline inflammation AD patients. Two of the patients tried the drink formulation, but did not continue while the other had been taking the drink formulation starting on Aug. 28, 2012.

Example 3

A study of the effect of an omega-3 drink containing antioxidants and resveratrol was conducted on patients with Alzheimer's disease, including some having mild disease, i.e., minor cognitive impairment. The patients are listed in the order as they enrolled into the study (Table 1). Most subjects were taking prescribed medication for Alzheimer disease, such as cholinesterase inhibitor and/or the NMDA inhibitor memantine. Cognitive state was examined by the Minimental State Examination (MMSE).

TABLE 1

Subjects in the study
A. Cognitively-impaired patient

| Patient # | Age, Sex | Initial MMSE score | Duration of memory problems before Smartfish supplementation (years) | Total duration of follow-up on Smartfish |
|---|---|---|---|---|
| 1 | 60, M | 19 | | 3.5 |
| 2 | 88, F | <5 | | 9 |
| 3 | 70, M | 24 | | 2 |
| 4 | 78, M | 23 | | 1 |
| 5 | 76, F | 6 | | 5 |
| 6 | 87, M | 11 | | 14 |
| 7 | 77, M | 30 | | 1 |
| 8 | 72, M | 26 | | 1 |
| 9 | 88, F | 16 | | 10 |
| 10 | 60, F | 26 | | 0.5 |
| 11 | 78, F | 29 | | 1 |
| 12 | 58, F | 8 | | |

Omega-3 drink with antioxidants: The subjects were taking daily 200 ml drink with 1,000 mg DHA, 1,000 mg EPA, botanical antioxidants. Since February 2014, the same drink was supplemented with resveratrol (75 mg/200 ml Smartfish drink) and 10 mcg vitamin D3 (Smartfish drink, Smartfish, Oslo, Norway).

Lymphocytes isolation and macrophage cultures: Heparinized blood from the AD patients was diluted with PBS (1:1 ratio; vol/vol). Peripheral blood mononuclear (PBMCs) cells were isolated from the diluted blood by Ficoll-hypaque gradient method at 2500 RPM for 20 minutes at room temperature, the mononuclear fraction was collected and washed two times with PBS, and cells were re-suspended with IMDEM medium. Macrophages were differentiated in 8-well chamber slides (Becton-Dickenson) from a seed of 50,000 mononuclear cells in IMDM medium with 10% autologous serum.

Flow cytometric FAM-Aβ phagocytosis assay: $0.5 \times 10^6$ PBMCs were suspended with IMDM medium with 10% autologous serum and were incubated with or without FAM-Abeta (Anaspec, San Jose, Calif.) overnight at 37° C. in 5% $CO_2$ incubator. The cells were then washed two times with FACS buffer and then labeled for 30 minutes at 4° C. with anti-CD14 PE. After incubation, cells were washed two times with FACS buffer and fixed with 1% paraformaldehyde. Flow cytometry was performed on FACSCalibur (Becton Dickinson) and FAM uptake was analyzed using FlowJo software (Ashland, Oreg.) with monocyte gate, based on forward and side scatter.

Figure 10A:
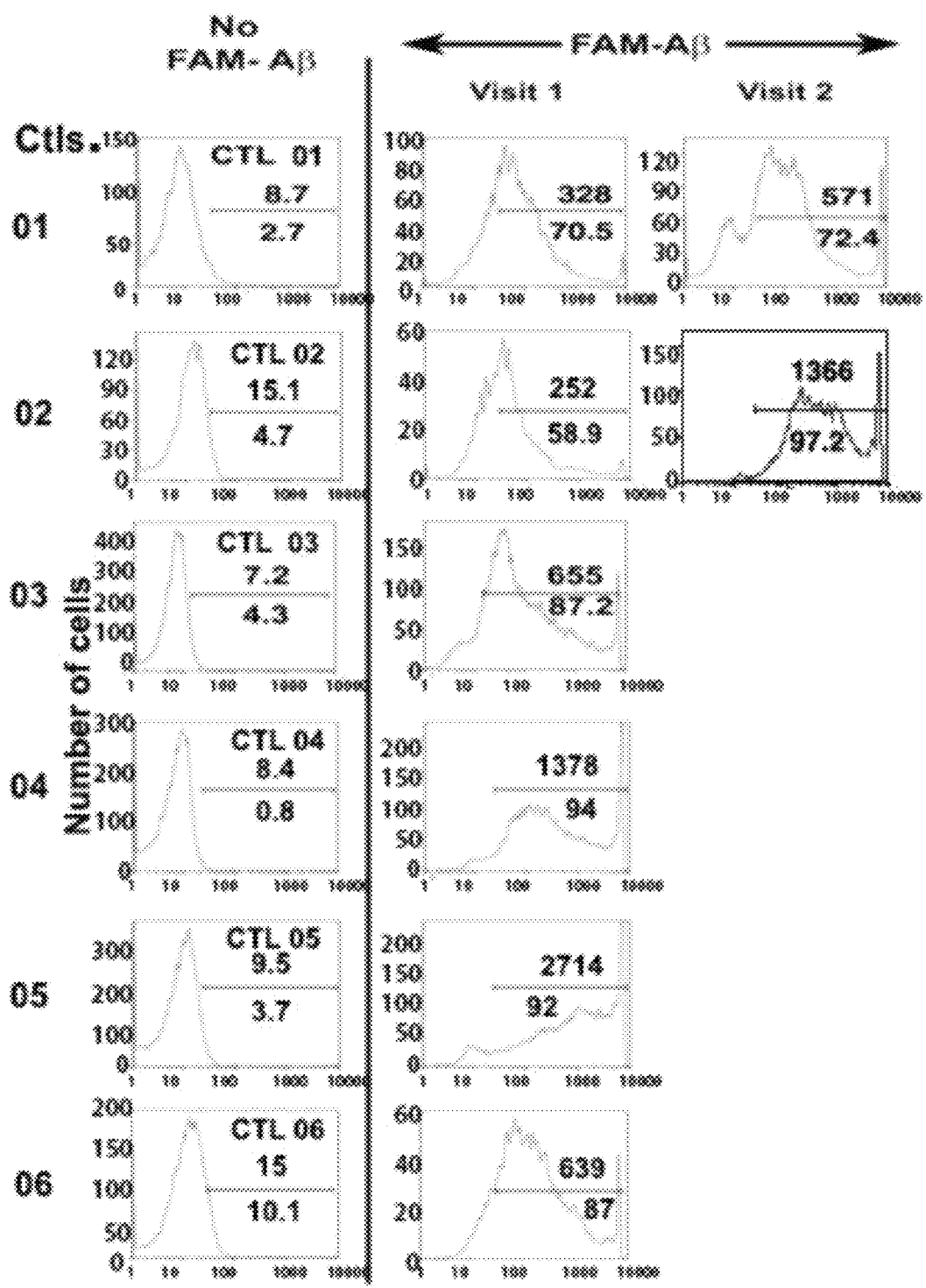
FIGS. 10A, 10B and 10C illustrate phagocytosis of FAM-amyloid-β by freshly isolated monocytes with the upper number in each graph being the mean fluorescence intensity of FAM-Aβ phagocytosis and the lower number in each graph is percent cells positive for Aβ.
Figure 10B:
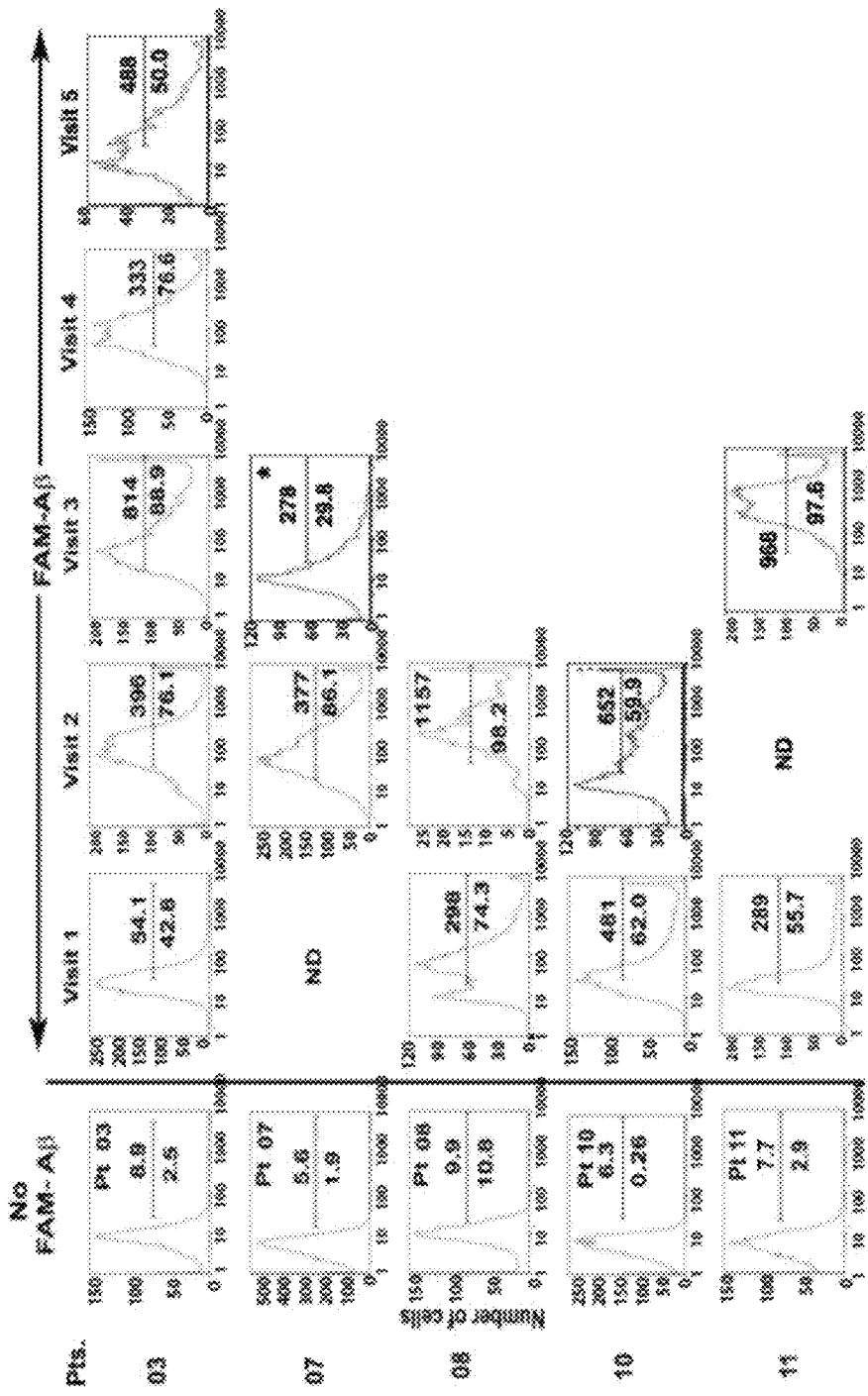
Figure 10C:
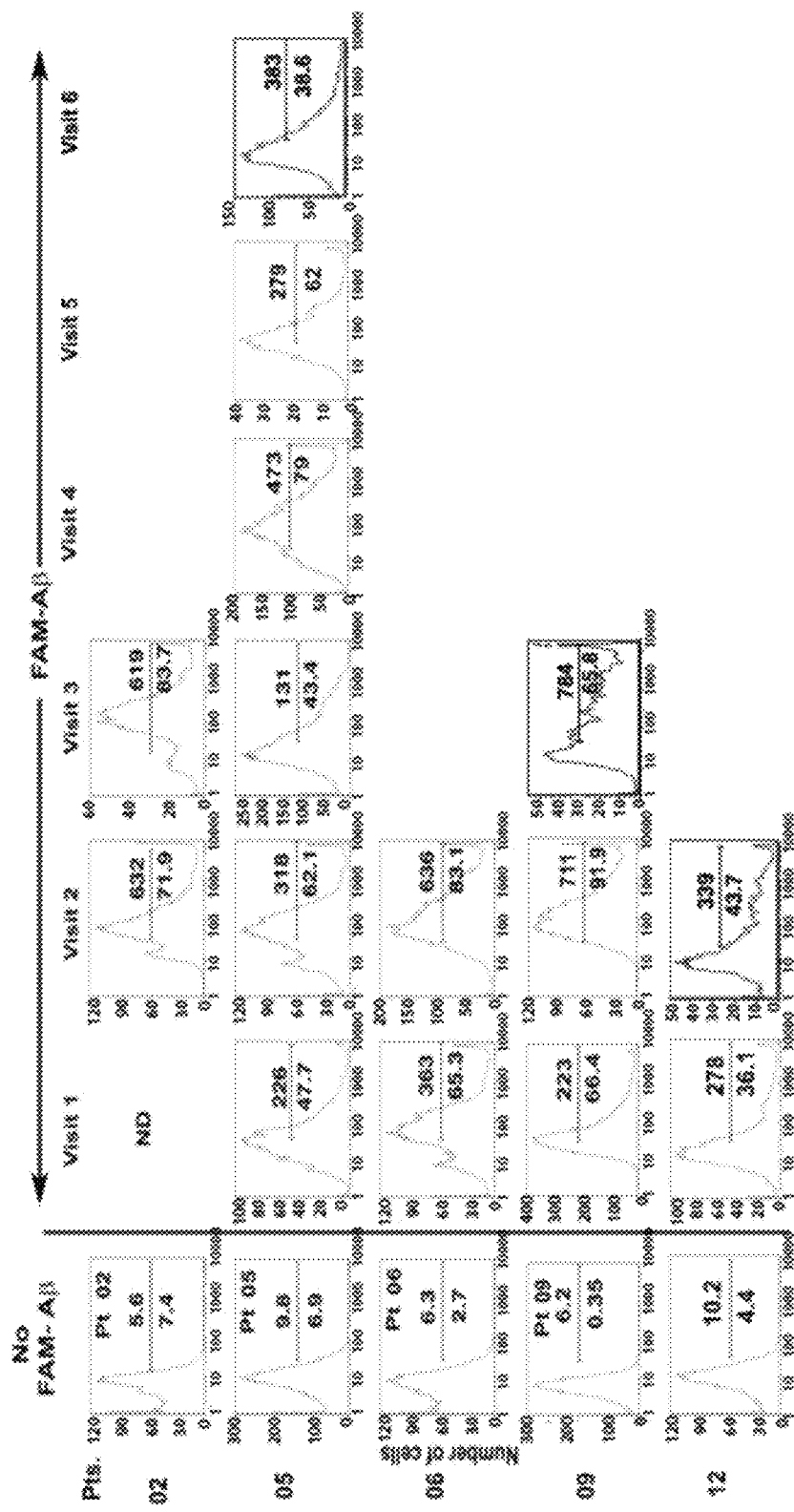

Results:

Amyloid-β phagocytosis by Blood Monocytes of AD Patients Taking ω-3 and Anti-Oxidants Aβ phagocytosis and cognition in AD patients taking the Smartfish drink (with resveratrol after February 2014) were prospectively studied (Table 2 and FIGS. 10B & 10C). The normal range of the Aβ phagocytosis test in cognitively-normal age-matched subjects was previously established as >450 MFI and in AD patients as ≤450 (Avagyan, Goldenson et al. 2009). The results in this study confirmed previous values at baseline. The mean score on the first visit (before ω-3 supplementation) was 272 MFI units in the group with advanced dementia (MMSE<19) and in the group with mild dementia or subjective memory complaints (MMSE≥19) was 280.5 (N.S.). In AD patients with advanced dementia taking nutritional supplementation with the drink Smartfish, the uptake of Aβ increased on the second visit to 574 MFI units; and in the patients with mild dementia the uptake increased to 643 MFI units. At baseline, cognitively normal subjects and patients with other neurological diseases were also tested (Table 2 and FIG. 10A).

immune system shown by amyloid-beta phagocytosis. The monocytes and, when tested, macrophages of AD patients before supplementation did not phagocytize Aβ when tested by immunofluorescence microscopy and the flow cytometric test. After the start of Smartfish supplementation, macrophages of AD patients, as early as after 19 days, showed effective uptake of FAM-Aβ. Because there were no patients in the intermediate range (MMSE 12-18), the effectiveness of omega-3 supplementation could not be defined in this group.

TABLE 2

MMSE and MFI Scores in patients on omega-3 supplementations

| MMSE Score at Baseline | Subject # | Duration of ALS (yrs) | MMSE | | | | | MFI units | | | | |
|---|---|---|---|---|---|---|---|---|---|---|---|---|
| | | | Visit 1 | Visit 2 | Visit 3 | Visit 4 | Visit 5 | Visit 1 | Visit 2 | Visit 3 | Visit 4 | Visit 5 |
| ≤18 | 2 | 6 | 4 | 4 | 4 | 4 | 4 | | 632 | 619 | | |
| | 5 | 3 | 6 | 7 | refused | 5 | | 226 | 318 | 131 | 473 | 279 |
| | 6 | 10 | 11 | 11 | | | | 363 | 636 | | | |
| | 9 | 10 | 16 | 16 | | | | 223 | 711 | | | |
| | 12 | 5 | 8 | | | | | 278 | | | | |
| | Mean | 6.8 | 9 | 9.5 | | 4.5 | | 272.5 | 574.2 | 375 | | |
| >18 | 1 | 3 | 19 | 22 | 23 | 18 | | | | | | |
| | 3 | 2 | 24 | 23 | 23 | | | 54.1 | 396 | 814 | | |
| | 4 | 1 | 23 | 30 | 30 | | | | | | | |
| | 7 | 1 | 30* | 30# | | | | | 377 | | | |
| | 8 | 1 | 26 | 30 | | | | 298 | 1157 | | | |
| | 10 | 0.5 | 26 | | | | | 481 | | | | |
| | 11 | | 29 | 30 | | | | 289 | | | | |
| | Mean | 1.21 | 25.28 | 27 | 25.33 | | | 280.5 | 643.3 | | | |

*Patient is complaining of "mental fog"
Patient is somewhat relieved of "mental fog"

Figure 11A:
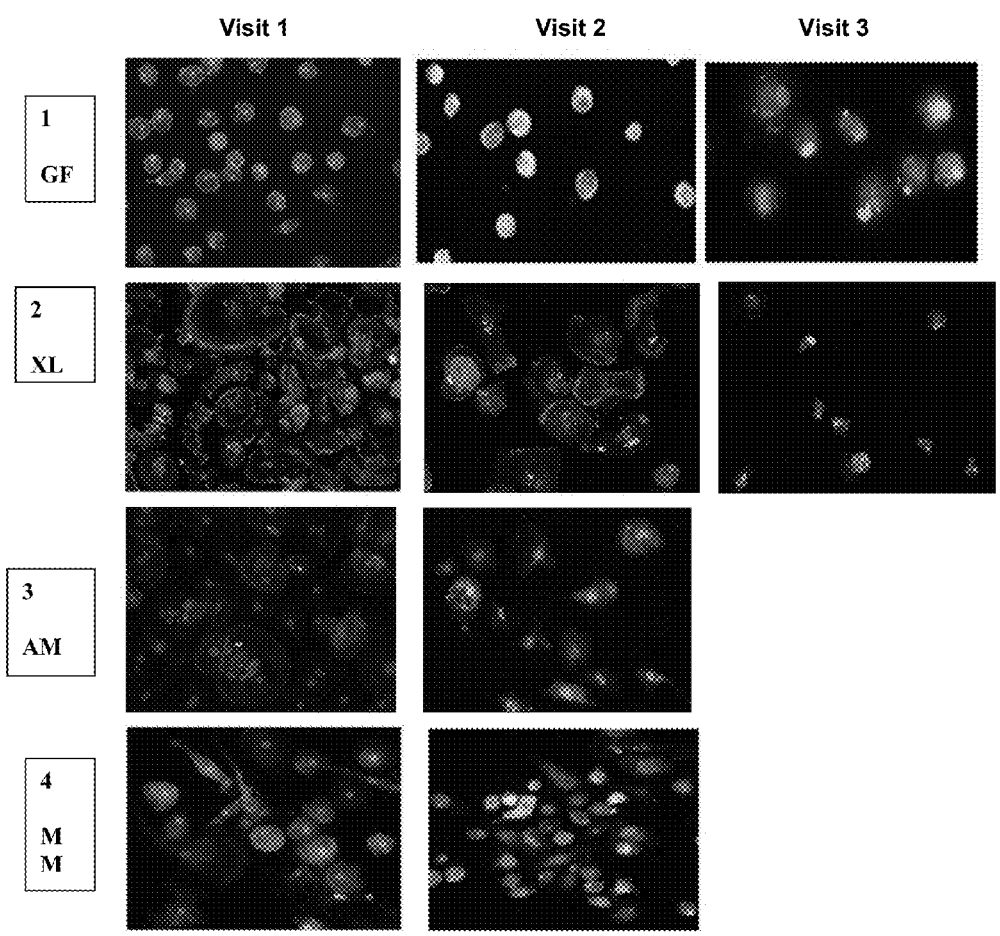
FIGS. 11A and 11B illustrate phagocytosis of FAM-Aβ by macrophages of AD patients on supplementation with the omega-3 drink with antioxidants supplemented with resveratrol (Smartfish drink) where visit 1 is before the Smartfish drink and visits 2 and 3 are after the Smartfish drink.
Figure 11B:
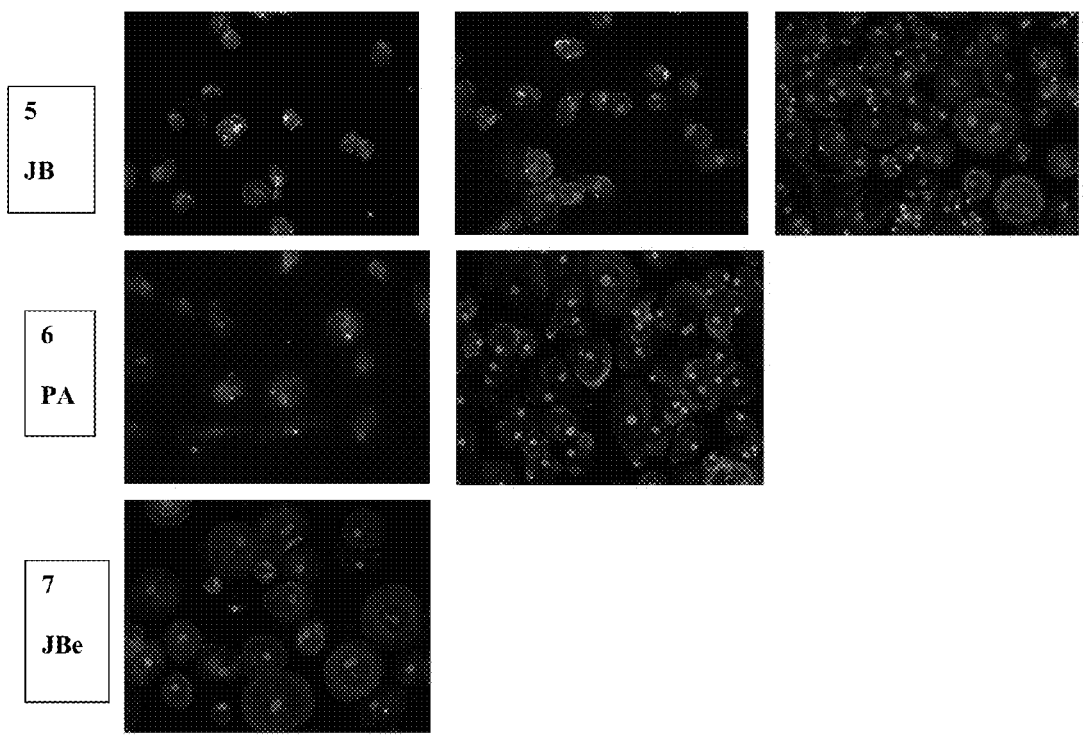

Phagocytosis of Amyloid-Beta by Macrophages of AD Patients Taking ω-3 and Anti-Oxidants PBMC's of AD patients were cultured for 10-15 days until macrophages became differentiated from monocytes. These macrophages were tested for Abeta phagocytosis by exposing them overnight to FAM-Abeta. In agreement with previous results, the macrophages of AD patients derived from the blood before the first visit were unable to phagocytize Abeta but macrophages isolated from the blood after omega-3 supplementation on subsequent visits improved phagocytosis in most subjects (FIGS. 11A & 11B).

Minimental State Examination (MMSE) Scores of AD Patients taking ω-3 and Anti-Oxidants In the group with advanced dementia (MMSE<19), the mean MMSE score before supplementation was 9.0 and the score did not significantly change after supplementation (mean score 9.5). In the group with mild cognitive impairment (MMSE≥19), the MMSE score increased from 23.8 to 27.5 after supplementation (Table 2).

Increase in Amyloid-β Phagocytosis by Resveratrol

Figure 12:
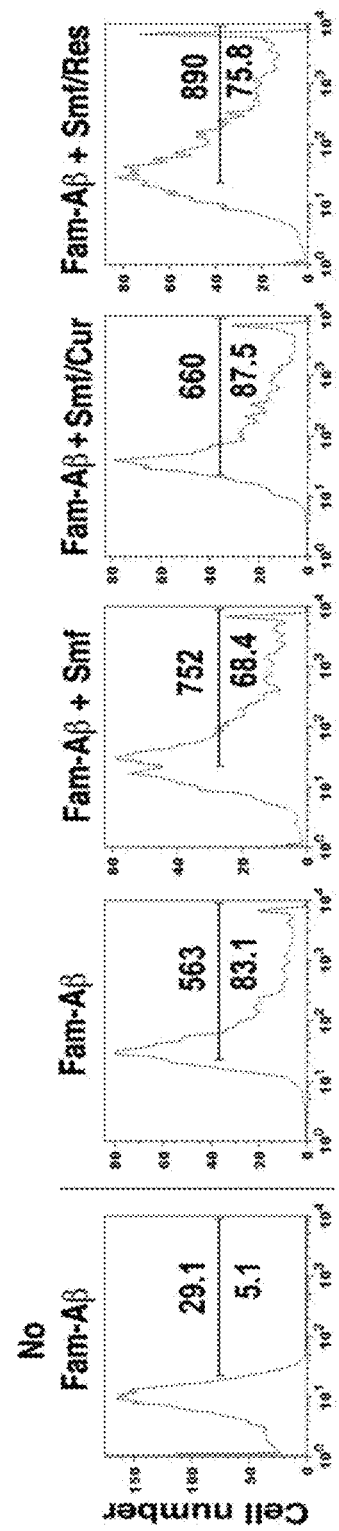
FIG. 12 illustrates the in vitro effect of curcumin and resveratrol in the omega 3/antioxidant emulsion on Aβ phagocytosis by macrophages of the AD patient #2. An increase in mean fluorescent intensity (MFI) (baseline MFI=563) an addition of Smartfish (MFI=752), Smartfish drink with curcumin (MFI=660), and Smartfish drink with 75 mg/200 ml resveratrol (MFI=890) was noted.

Resveratrol was shown to promote proteasome degradation of amyloid-beta in cell lines (Marambaud, Zhao et al. 2005). The in vitro activity of Smartfish drink, Smartfish drinks with curcumin and Smartfish drink with 75 mg/200 ml resveratrol on phagocytosis of amyloid-beta by monocytes. The mono nuclear cells of the AD patient #2, were tested overnight by the Aβ assay with Smartfish, Smartfish/curcumin or Smartfish/resveratrol. The phagocytosis was maximal with Smartfish/resveratrol (FIG. 12).

Discussion

The key result of this study showed that most AD and MCI patients supplemented with omega-3 improved their The flow cytometric Aβ test is a sensitive and specific (except for care givers) biomarker of AD and MCI, and may be a useful test for following patients receiving immunosupportive nutritional therapies, such as omega-3, vitamin D, curcuminoids, phospholipids, uridine, etc, or other immunomodulating therapies, such as Aβ vaccine or antibodies. A low result in the Aβ test may be both a biomarker of early disease and a worry of need for omega-3 and antioxidant supplementation. The test may be useful in many conditions where omega-3 have potential health benefits, including AD, cardiovascular conditions (Harris and Von Schacky 2004) (de Oliveira Otto, Wu et al. 2013), neuropsychiatric disorders, including depression and dementia (Riediger, Othman et al. 2009), inflammation (Calder 2006), and cancer (Gleissman, Johnsen et al. 2010).

TABLE 3

Resolvin D1 produced by macrophages of the ALS patient #5 before and after omega-3 supplementation

| Patient # | Date | Supplementation with ω-3 (days) | Resolvin D1 (pg/ml) in macrophages from patients | |
|---|---|---|---|---|
| | | | DHA not added in vitro | DHA added in vitro |
| 5 | Nov. 1, 2013 | none | 0 | 0 |
| | Dec. 5, 2013 | 35 | 8 | 13.6 |
| | Mar. 4, 2014 | 124 | 21.3 | 28.6 |

While cognitive benefits are difficult to evaluate in a small study, the followup tests in this study showed consistently positive effects with stabilization even improvement of MMSE in patients with early dementia when treated with an omega-3 drink containing antioxidants and resveratrol.

What is claimed is:

1. A method of treating a patient with Alzheimer's disease comprising administering a formulation to the patient, the formulation comprising; (i) a fresh marine oil in an oil-in-water emulsion, wherein the marine oil has a totox value below 15; and (ii) resveratrol or C1-C6 alkyl ester derivatives thereof,
   wherein the marine oil is present in about 0.5% to about 10% by weight of the formulation and the resveratrol is present in about 0.01% to about 0.5% by weight of the formulation, and wherein the formulation is a drink formulation further comprising fruit juice concentrate.

2. The method of claim 1, wherein the formulation further comprises Vitamin $D_3$.

3. The method of claim 2, wherein the formulation is administered on a daily basis.

4. A method of delaying the onset of symptoms associated with Alzheimer's disease comprising administering a formulation to a person, the formulation comprising: (i) a fresh marine oil in an oil-in-water emulsion, wherein the marine oil has a totox value below 15; and (ii) resveratrol or C1-C6 alkyl ester derivatives thereof,
   wherein the marine oil is present in about 0.5% to about 10% by weight of the formulation and the resveratrol is present in about 0.01% to about 0.5% by weight of the formulation, and wherein the formulation is a drink formulation further comprising fruit juice concentrate.

5. The method of claim 4, wherein the formulation further comprises Vitamin $D_3$.

6. The method of claim 5, wherein the formulation is administered on a daily basis.

7. The method of claim 4, wherein the person has been diagnosed with Alzheimer's disease.

8. The method of claim 4, wherein the person has not been diagnosed with Alzheimer's disease.

9. The method of claim 3, wherein administering on a daily basis is once daily.

10. The method of claim 6, wherein administering on a daily basis is once daily.

11. The method of claim 1, wherein the drink formulation has a volume in a range of 50 to 300 ml.

12. The method of claim 4, wherein the drink formulation has a volume in a range of 50 to 300 ml.

13. The method of claim 1, wherein the fruit juice concentrate is selected from the group consisting of apple juice concentrate, pear juice concentrate and mixtures thereof.

14. The method of claim 2, wherein the drink formulation further comprises pomegranate and/or chookberry.

15. The method of claim 1, wherein the drink formulation further comprises vitamins selected from the group consisting of Vitamin D, Vitamin C, Vitamin B and mixtures thereof.

16. A method of treating a patient with Alzheimer's disease comprising administering a drink formulation to the patient, the formulation comprising: (i) a fresh marine oil in an oil-in-water emulsion in an amount of about 0.5% to about 10% by weight, wherein the marine oil has a totox value below 15; (ii) resveratrol or C1-C6 alkyl ester derivatives thereof in an amount of about 0.01% to about 0.5% by weight; (iii) fruit juice concentrate; and (iv) one or more vitamins.

17. A method of delaying the onset of symptoms associated with Alzheimer's disease comprising administering a drink formulation to a person, the formulation comprising: (i) a fresh marine oil in an oil-in-water emulsion in an amount of about 0.5% to about 10% by weight, wherein the marine oil has a totox value below 15; (ii) resveratrol or C1-C6 alkyl ester derivatives thereof in an amount of about 0.01% to about 0.5% by weight; (iii) fruit juice concentrate; and (iv) one or more vitamins.

18. The method of claim 17, wherein the person suffers from minor cognitive impairment.

19. The method of claim 4, wherein the person suffers from minor cognitive impairment.

20. The method of claim 4, wherein the fruit juice concentrate is selected from the group consisting of apple juice concentrate, pear juice concentrate and mixtures thereof.

21. The method of claim 5, wherein the drink formulation further comprises pomegranate and/or chookberry.

22. The method of claim 4, wherein the drink formulation further comprises vitamins selected from the group consisting of Vitamin D, Vitamin C, Vitamin B and mixtures thereof.

* * * * *